United States Patent [19]
Eckerson

[11] Patent Number: 4,865,048
[45] Date of Patent: Sep. 12, 1989

[54] METHOD AND APPARATUS FOR DRUG FREE NEUROSTIMULATION

[76] Inventor: Harold D. Eckerson, P.O. Box 432, Sag Harbor, N.Y. 11963

[21] Appl. No.: 139,967

[22] Filed: Dec. 31, 1987

[51] Int. Cl.$^4$ .............................................. A61N 1/00
[52] U.S. Cl. .................................... 128/791; 128/421
[58] Field of Search .................... 128/380, 419 S, 791, 128/421, 422, 423, 802; 600/26

[56] References Cited

U.S. PATENT DOCUMENTS

| | | | |
|---|---|---|---|
| 3,762,396 | 10/1973 | Ballentine et al. | 128/422 |
| 4,018,218 | 4/1977 | Carlson et al. | 128/422 |
| 4,503,863 | 3/1985 | Katims | 600/26 |
| 4,646,744 | 3/1987 | Capel | 128/423 R |
| 4,709,700 | 12/1987 | Hryman | 128/419 S |
| 4,724,841 | 2/1988 | Kastnbin et al. | 128/791 |

Primary Examiner—Max Hindenburg
Assistant Examiner—Scott Getzow
Attorney, Agent, or Firm—Michael I. Kroll

[57] ABSTRACT

A medical method and apparatus consisting of a belt worn battery operated waveform generator is provided to give patients suffering from drug or alcohol withdrawal relief from severe physical symptoms associated with the initial abstinence from the drug to which they are addicted. The instant invention in principal is an advanced and more sophisticated form of electro acupuncture which rather than delivering some arbitrary electric current delivers a non-invasive and very specific electromagnetic waveform to the patient's mastoid processes behind the ear using two electrodes attached to the waveform generator. After approximately forty minutes the symptoms associated with the acute drug or alcohol withdrawal are either significantly reduced or are completely eliminated. In use, the device is typically worn by the patient during an initial three to five day abstinence period and the patient may alter the intensity of stimulation and duration of stimulation. Importantly, during stimulation the patient feels no discomfort, is totally mobile, and, since the electrodes do not pierce the skin, risk of infection or transmission of blood born infectious diseases is impossible. In addition to reducing the physical symptoms of withdrawal the method also decreases the total time of clinical and sub-clinical withdrawal state that is associated with initial abstinence from drug dependence as compared to standard therapies such as methadone substitution.

7 Claims, 2 Drawing Sheets

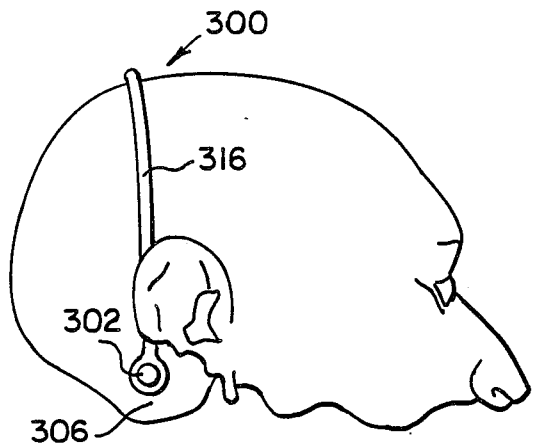
Figure 1
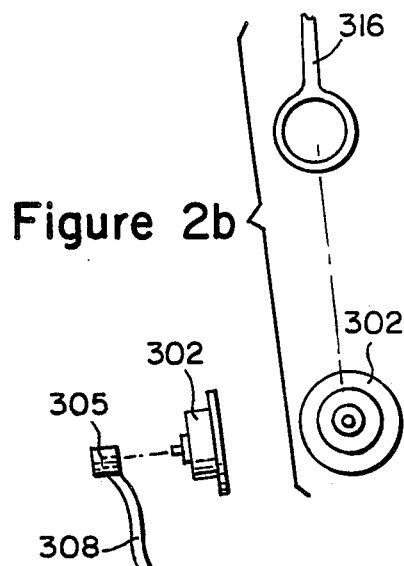
Figure 2b
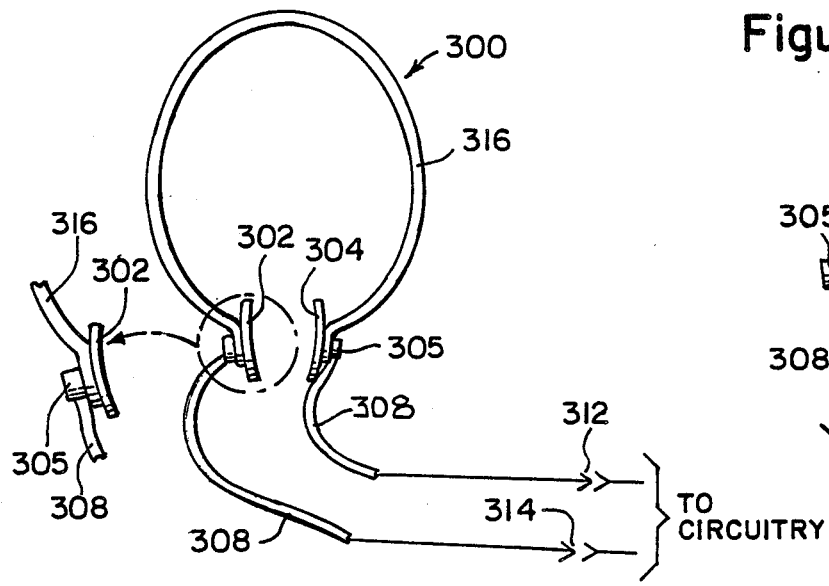
Figure 2a
Figure 2

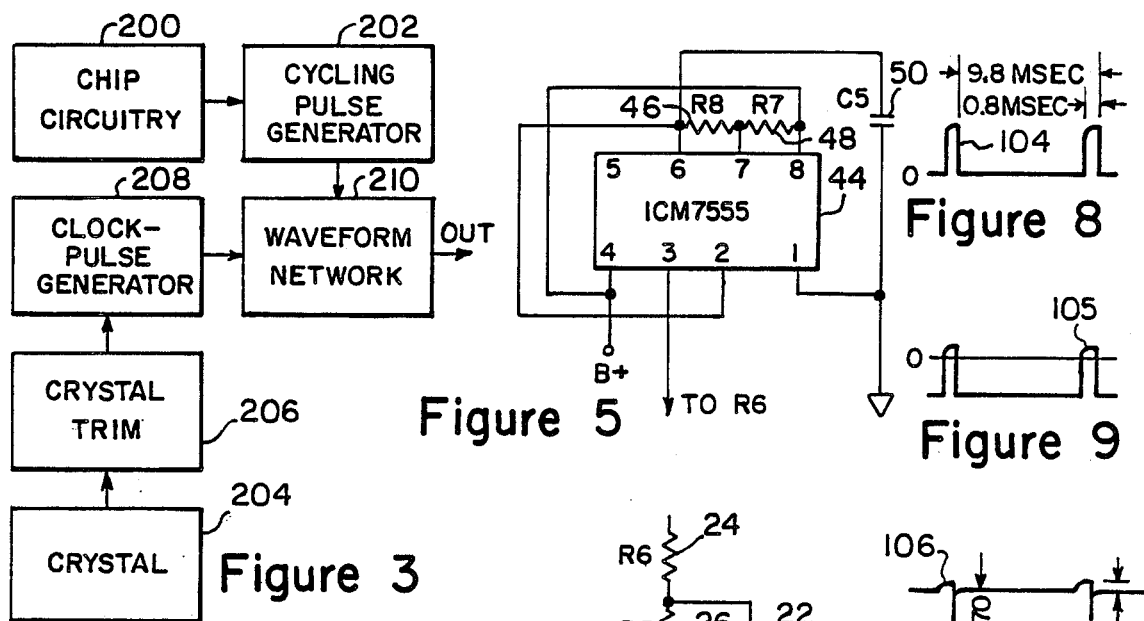
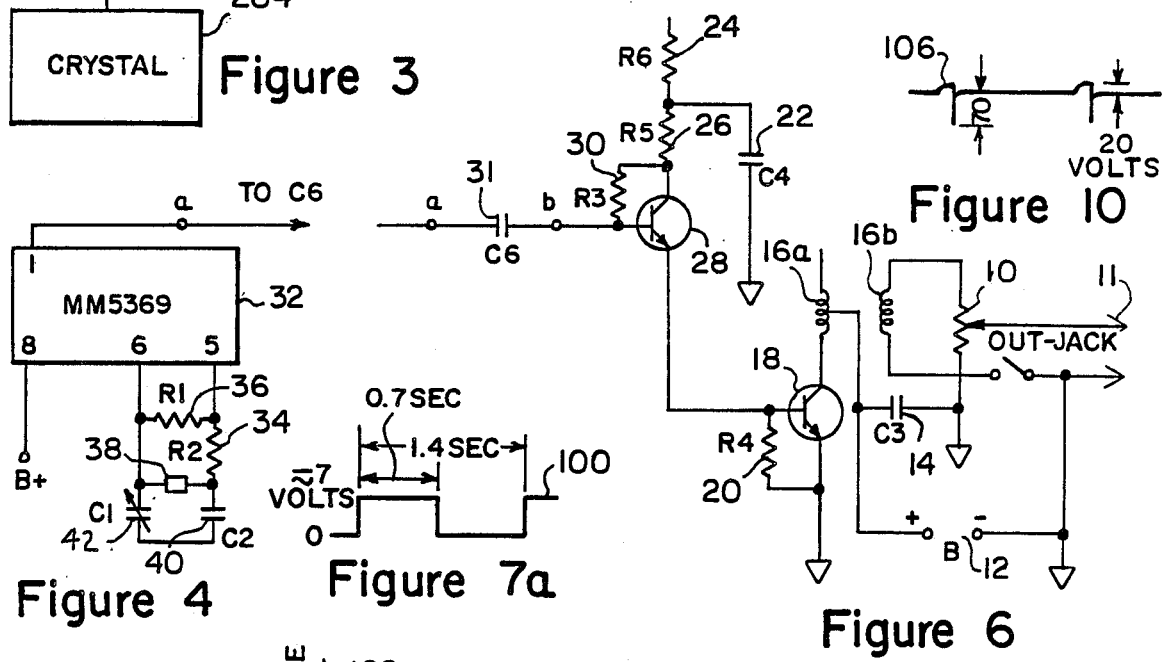
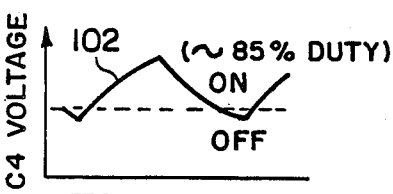
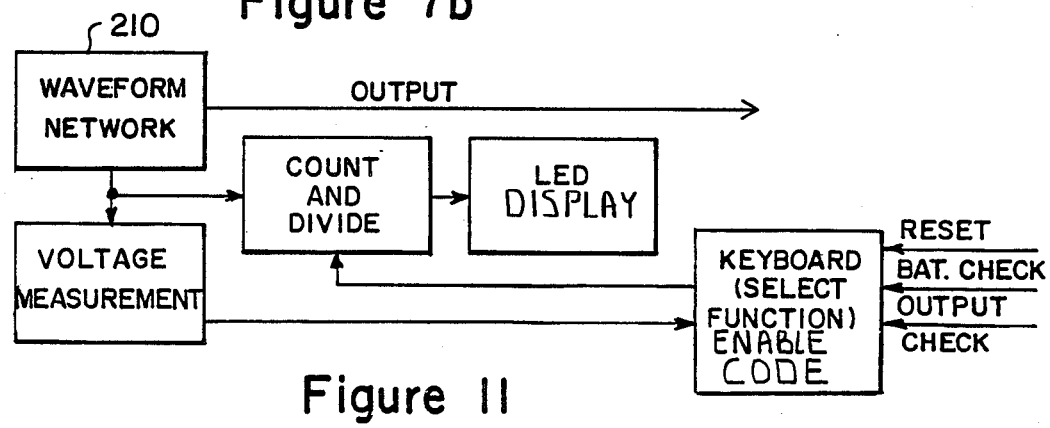

METHOD AND APPARATUS FOR DRUG FREE NEUROSTIMULATION

BACKGROUND OF THE INVENTION

1. Field of the Invention

The instant invention relates generally to the field of drug and alcohol withdrawal symptom alleviation, and, more specifically, to the method and use of biologically applied electrical signals to relieve suffering from narcotic withdrawal.

2. Description of the Prior Art

Drug and alcohol addiction is a major problem throughout the world, especially in the U.S. Some sources quote 10% of the U.S. population as being addicted to either drugs or alcohol. The problem is becoming worse and is fast becoming a political as well as an economic and medical issue. The biochemical basis of addiction involves the body's natural opiate-like pain killers which are secreted by the brain cells into the nervous system. These have become known generically as the endorphins and the enkephalins. Many different types have been identified to date and they interact in complex ways, which have yet to be fully elucidated, with neurons. In structure and function these endorphins resemble the opiate drugs of addiction like heroin and cocaine and are also known to be involved in all compulsive addictive type behaviors including alcoholism, smoking, and overeating.

Heroin addicts, for example, take into their bodies an exogenous source of opiates which severely interferes with the endorphin/enkaphalin system. When this external source is interrupted severe withdrawal symptoms ensue. This withdrawal state has been associated with low levels of the body's normal endogenous endorphins and altered ratios of different types of endorphins and enkephalins. This has been caused by the previous involvement of the heroin or other drug of addiction in the physiological processes. It is this low and abnormally functioning endorphin level that causes the symptoms of acute withdrawal. This withdrawal state persists until the body has had a chance to normalize this system which takes on average 3-4 days. This acute withdrawal state if left untreated is known as going "cold turkey".

Standard methods of getting patients through this withdrawal state, i.e. of detoxifying them, in general use the principal of drug substitution and gradual weaning from the substitute drug, e.g. methadone, in the case of heroin, and Valium in the case of alcoholics. Many addicts only get to the state of substitution and never get weaned off the methandone, hence the large number of methadone clinics in the United States and Europe. The best that these patients can expect is that they may be able to function better and live longer on methadone. The vast majority of addicts return to their addictions following detoxification, hence the persistent and relentless nature of the problem.

Withdrawal symptoms consist of two main types corresponding with the two major subdivisions of the human nervous system. Symptoms are associated with the somatosensory nervous system and the autonomic nervous system. The somatosensory nervous system is the main one of which we are aware which senses our environment, position and well being of our bodies, and also senses pain. The autonomic nervous system controls the "automatic" functions of life, i.e. the functions of organs like the heart, sweat glands, etc. Withdrawal symptoms associated with the somato-nervous system include joint pains and muscle cramps which can be extremely severe. The autonomic symptoms include nauses, vomiting, cold sweats, gooseflesh, and signs such as markedly dilated eye pupils. A third group of symptoms common to withdrawal from all addictions and compulsive behavior is anxiety and craving.

Application of the present invention to patients who have just entered this withdrawal phase of detoxification following abstinence from their drug of addiction causes a cessation of all these symptoms in a period of about 40 minutes.

The specific low frequency electromagnetic waveform affects the production and function of the endorphins and enkephaline in such a way as to return them to normal and alleviate the symptoms of acute withdrawal. Clinical data using the present invention has shown that it can alleviate severe withdrawal symptoms in a period of 40 minutes. The patient then uses the device for a period of 3-5 days, basically deciding for himself the amount of time he requires the device to be active for. During this period patients do not require any other forms of medication to deal with their withdrawal symptoms. As the patient experiences such a painless detoxification process and is rendered drug free, clinical data suggests that the recidivism rate in patients treated by this method may be much lower than the standard therapeutic approach.

SUMMARY OF THE INVENTION

It is, therfore, a primary object of the present invention to provide a drug free neurostimulation method and device (NSD) that provides a 3 to 5 day treatment designed to precipitously reduce both acute and chronic withdrawal symptomalology of all addictive chemical substances, without drugs and with virtually no negative side effects. The NSD acts by specific electrical frequency stimulation of endorphin production that has previously been decreased due to chronic substance abuse.

Another object is to provide a drug free neurostimulation method and device (NSD) that is compact and is affixed to the belt of a patient, and is utilized intermittently on a daily basis for approximately 3 to 5 days. The NSD unit is designed for simple applications by physicians, nurses and patients.

A still further object is to provide a drug free neurostimulation method and device that can be completely programmed to either treat a particular drug or addiction or a combination of simultaneous addictions; and requires minimal supervision by a physician or nurse.

The following is a classification of the principal withdrawal symptoms that patients experience after prolonged use of narcotic agents or a mixture of narcotics and alcohol:

Type 1. Central nervous system (somato-sensory) symptoms such as restlessness, irritability, muscle aches, yawning and severe, prolonged insomnia;

Type 2. Symptoms mediated through autonomic nervous system, such as running nose, over-breathing, abdominal cramps, vomiting and diarrhea; and, Type 3. Two symptoms common to all drugs of dependence: anxiety and craving for the drug.

The NSD Unit electrodes are placed behind the ear on the mastoid processes in close proximity to stimulate a branch of the vagus nerve, a major component of the autonomic nervous system.

A still further object, therefore, is to provide a drug free neurostimulation method and device that by retrograde stimulation similar in principle to electroacupuncture, alleviates Type 2 symptoms.

A yet further object is to provide a drug free neurostimulation method and device that alleviates Type 1 symptoms by using electromagnetic waves to stimulate the brain cells to restart their normal production of endorphins which have, in the addict, been altered or repressed.

Another yet further object is to provide a drug free neurostimulation method and device that alleviates Type 3 symptoms by a probable direct affect on the brain, in particular, on a part of the brain termed the Corpus Striatum that contains the majority of opiate receptors, and when interfered with electrochemically by the neurostimulator, alleviates symptoms of anxiety and craving.

A still further object is to provide a drug free neurostimulation method and device (NSD) that delivers a very specific electromagnetic waveform known to be effective in this case for narcotic, or drug addiction, used with or without alcohol.

This highly specific waveform is generated from a battery operated, calculator sized generator which is attached to the patient's belt. The generator is attached by two leads to two surface electrodes which are placed on the patient's mastoid processes behind the ears. Following a period of 40 minutes the symptoms associated with acute narcotic withdrawal are alleviated or significantly reduced.

The present invention is worn by a patient during the initial 3–5 days of abstinence. The patient may alter the intensity of stimulation themselves, and in general, they decide the length of the periods of stimulation they require each day. During periods of stimulation the patient feels no discomfort and is totally mobile.

The electrodes do not pierce the skin and so there is no chance of infection or transmission of blood born infectious diseases. In addition to reducing the physical symptoms of withdrawal, the present invention is known to decrease the total time of the clinical and sub-clinical withdrawal state associated with the initial abstinence from drugs of dependence. This is observed by comparing the withdrawal period with that associated with standard therapies such as methadone substitution therapy.

It is, therefore, a still further object to provide a drug free neurostimulation method and device that produces a symptomless, shorter detoxification process and a lower recidivism rate.

Further objects of the invention will appear as the description proceeds.

To the accomplishment of the above and related objects, the present invention may be embodied in the form illustrated in the accompanying drawings, attention being called to the fact, however, that the drawings are illustrative only and that changes may be made in the specific construction illustrated and described within the scope of the appended claims.

BRIEF DESCRIPTION OF THE DRAWING FIGURES

The figures in the drawings are briefly described as follows:

FIG. 1 of the drawing depicts the electrode harness in place on a patient's head in the process of neurostimulation.

FIG. 2 of the drawing depicts the electrode harness connected to the output of the circuitry.

FIG. 2a of the drawing is a side view of one of the electrodes exploded from the wire snap-on connector.

FIG. 2b of the drawing is a front view of one of the electrodes exploded from the retainer hole in the tension band.

FIG. 3 of the drawing is an electronic block diagram of the circuitry involved in the present invention.

FIG. 4 of the drawing is an electronic schematic diagram showing crystal oscillator and divider, and trimmer components of the preferred embodiment of the present invention.

FIG. 5 of the drawing is an electronic schematic diagram showing the cycling-pulse generator component of the preferred embodiment of the present invention.

FIG. 6 of the drawing is an electronic schematic diagram showing the waveform network component of the preferred embodiment of the present invention.

FIG. 7a of the drawing illustrates the voltage present at the output pin 3 of the cycling-pulse generator depicted in FIG. 5.

FIG. 7b of the drawing illustrates the voltage present across capacitor C4 of the waveform network depicted in FIG. 6.

FIG. 8 of the drawing illustrates the voltage present at output pin 1 of the circuit depicted in FIG. 4.

FIG. 9 of the drawing illustrates the voltage present after capacitor C6 of the circuit depicted in FIG. 6.

FIG. 10 of the drawing illustrates the output waveform.

FIG. 11 is a block diagram showing a typical assortment of monitoring functions to assist in standardized application of the circuitry in patient care.

DETAILED DESCRIPTION OF THE PREFERRED EMBODIMENTS

In FIGS. 1 through 2b, the electrode harness 300 places electrodes 302 and 304 against the patient's mastoid processes, typified by 306. Electrodes 302 and 304 are connected to wire snap-on connectors 305 on wires 308 and 310 to the output of the circuitry via plugs 312 and 314 respectively. Electrodes 302 and 304 are held in place by tension-band 316.

The generation of the therapeutic electrical waveform is best understood with reference to FIG. 3 through FIG. 10. The apparatus shown is the preferred embodiment for generating the requisite waveform, however other circuit configuration are possible within the scope of the present invention.

The electronic block diagram of FIG. 3 combines all the functional blocks illustrated in detail in FIGS. 4, 5, and 6.

The circuit illustrated in FIG. 4 is used to generate the voltage illustrated in FIG. 8 (104). An oscillator/divider chip 32, typified by the commercially available chip MM5369, uses a piezoelectric crystal 38 as well as resistors R1 (34) and R2 (36) and capacitors C2 (40) and C1 (42). The repetition rate of the positive pulse train from the output at pin 1 may be varied by adjusting the trim circuitry (C1 is shown as a variable capacitor) or by changing the frequency of crystal 38. Typically, the pulse width at the output is one millisecond and the repetition rate is 100 Hertz. The crystal shown as numeral 38 in FIG. 4 is represented as box 204 in FIG. 3. The variable capacitor C1 (42) together with C2 (40) and resistors R1 (34) and R2 (36) in FIG. 4 are represented as crystal trim 206 in FIG. 3. The chip MM5369 shown as numeral 32 in FIG. 4 is represented as clock-pulse generator 208 in FIG. 3.

The circuit illustrated in FIG. 5 is used to generate the voltage shown in FIG. 7a (100). This cycling pulse generator uses a conventional timing chip 44, typified by commercially available chip ICM7555. The repetition rate of the output from pin 4 is determined by resistors R8 (46), R7 (48), and capacitor C5 (50). In the instant invention this voltage 100 has a typical amplitude of 7 volts, on and off for equal durations, and a pulse repetition rate of typically 1.4 seconds. Chip 44 in FIG. 5 is represented as cycling pulse generator 202 in FIG. 3 while resistors R8 (46), R7 (48), and capacitor C5 (50) are represented as chip circuitry 200 in FIG. 3.

The circuit illustrated in FIG. 6 is used to generate the output waveform 106 shown in FIG. 10. The waveform network uses a pair of NPN transistors 28 and 18 connected as a modified Darlington pair. The clock pulse 104 of FIG. 8 is coupled via capacitor C6 (31) to the base of transistor 28. R3 (30) serves in base bias position. Voltage 100 of FIG. 7a is coupled to the collector of transistor 28 through an RC network comprising R6 (24), R5 (26), and capacitor C4 (22). The time constant of this RC network is chosen to produce the sawtooth waveform 102 illustrated in FIG. 7b. This waveform turns transistor 28 on and off with approximately an 85-90 percent duty cycle.

Transistor 18 stands in emitter-follower position to transistor 28. Resistor R4 (20) places the transistor 28 output across base-emitter of transistor 18.

The collector output of transistor 18 is coupled via transformer with primary winding 16a and secondary winding 16b. Capacitor C3 (14) provides bypassing. The gradually increasing, positive portion of the leading edge of the clock pulse after C6 (see FIG. 9) results in gradually increasing currents and voltages in the transformer windings, the voltages being proportional to the rate of change of current with time ($V = L\, di/dt$). At the sharp trailing edge of the clock pulse the current shut-down is very sudden, resulting in an induced voltage 105 greater than the first, of shorter duration, and opposite polarity. The typical output waveform 106, before control by potentiometer, before losses in transmission lines to electrodes, and before losses in coupling between electrode and patient, has a pulse width of 1 millisecond, a positive pulse amplitude of 20 volts, a negative spike amplitude of minus 70 volts, a pulse repetition rate of 100 Hertz, and is gated on and off with a duty cycle of about 85%. The waveform network illustrated on FIG. 6 is represented by waveform network 210 in FIG. 3.

The output of transformer secondary 16b is coupled through potentiometer 10 to a switched output jack 11 so that the electrode harness 300 can be plugged in. The negative connection of battery 12 is switched by output jack 11 so that power is only supplied to the device when a plug is inserted into output jack 11.

FIGS. 3 through 10 throughout, and particularly FIG. 6 distinguish between chassis ground and a battery ground (negative) which are made common to place the circuit in operation. These grounds are common points internal to the circuitry and they are never connected to an outside grounding system. From the point of view of the patient, there is nothing to distinguish between the two leads from the circuitry to the electrodes except that they carry waveforms of relatively opposite polarity. When a waveform of one polarity is applied to one mastoid process, a waveform of opposite polarity is applied to the other.

FIG. 11 shows in block form a typical assortment of momitoring functions to assist in standardized administration of patient care. Final specification of functions to be monitored- and implementing circuitry- await completion and evaluation of current clinical trails. They will be of standard type, but are illustrated since the the present application concerns the complete clinical method.

While certain novel features of this invention have been shown and described and are pointed out in the annexed claims, it will be understood that various omissions, substitutions and changes in the forms and the details of the device illustrated and in its operation can be made by those skilled in the art without departing from the spirit of the invention.

LIST OF COMPONENTS 10. output potentiometer
11. output jack with switch
12. battery, 9 volts
14. capacitor, bypass
16a. transformer primary
16b. transformer secondary
18. NPN transistor
20. resistor
22. capacitor
24. resistor
26. resistor
28. NPN transistor
30. resistor
31. capacitor
32. oscillator/divider chip,
34. resistor
36. resistor
38. piezoelectric crystal
40. capacitor
42. variable capacitor
44. timing chip,
46. resistor
48. resistor
50. capacitor
100. voltage, cycling generator
102. voltage, C4 sawtooth waveform
104. voltage, clock pulse; T=9.8; f=102 Hz
105. voltage, after capacitor
106. output waveform
200. chip circuitry
202. cycling pulse generator
204. crystal
206. crystal-trim
208. clock-pulse generator
210. waveform network
300. electrode harness
302. electrode
304. electrode
305. wire snap-on connector
306. mastoid process
308. wire
312. plug
314. plug
316. tension-band

What is claimed is:

1. A method of relieving a patient's suffering due to narcotic and alcohol withdrawal, which comprises:
   a. applying a train of electrical pulses to the patient's mastoid processes, said electrical pulses comprised of square waves and spikes being applied to each of said mastoid processes simultaneously, said square waves and spikes being applied to each of said mastoid processes with opposite polarity, said square waves electrical pulses having a pulse width of one millisecond and an amplitude, at the source, of 20 volts and lower and a pulse repetition rate of 100 Hertz, said electrical spikes have an amplitude, at the source, of seventy volts with a polarity opposite to said square wave puleses wherein a spike pulse follows immediately upon the conclusion of each of said square wave pulses; and b. controlling the waveform and frequency of said pulses.

2. A method of relieving a patient's suffering due to narcotic and alcohol withdrawal, as recited in claim 1, wherein said train of electrical pulses is alternately turned on and off with a duty cycle of eighty-five percent.

3. A drug free neurostimulator, which comprises:
a. electrodes for applying a train of electrical pulses to the mastoid processes of a patient, said train of electrical pulses comprises individual pulses with an amplitude of 20 volts and a pulse width of one millisecond, followed immediately by a voltage spike of opposite polarity with an amplitude of 70 volts, wherein said pulses have a pulse repetition rate of 100 Hertz, with both voltage magnitudes measured at the source;
b. an electrode harness being in electrical communication with said electrodes and carrying said train of electrical pulses to said electrodes; and
c. means for generating a train of electrical pulses carried by said electrode harness to said electrodes so that by the application of said electrical pulses to said mastoid processes, a patient's suffering due to narcotic and alcohol withdrawal is relieved.

4. A drug free neurostimulator, as recited in claim 3, wherein said train of electrical pulses is alternately turned on and off with a duty cycle of eighty-five percent.

5. A drug free neurostimulator, as recited in claim 3, wherein said means for generating a train of electrical pulses carried by said electrode harness to said electrodes comprises a crystal-controlled oscillator and divider to generate positive going pulses with a pulse width of one millisecond and a pulse repetition rate of 100 Hertz, a cycling-pulse generator to generate a square wave with a pulse width of 0.7 seconds, and a waveform network whose inputs are: said positive going pulses and said square wave; and whose output is a pulse train comprising: pulses with a pulse width of one millisecond, and an amplitude of 20 volts, followed immediately by a spike of opposite polarity with an amplitude of 70 volts; wherein said pulse train is alternately turned on and off with a duty cycle of eighty-five percent.

6. A drug free neurostimulator, as recited in claim 10, wherein said waveform network comprises a transistor pair wherein positive clock pulses are coupled to the base input of a first stage, said square wave is coupled via a resistor-capacitor network to the collector of said first stage, and the output of a second stage is transformer coupled to said electrode harness, such that both waveform network inputs present a high impedance to reduce waveform distortion, while the output of the final stage is presented to said electrode harness.

7. A drug free neurostimulator, as recited in claim 6 further comprising a potentiometer connected between the output of said waveform network and said electrodes, wherein said potentiometer is used to vary the intensity of stimulation of said patient's mastoid processes.

* * * * *